US006544484B1

(12) United States Patent
Kaufman et al.

(10) Patent No.: US 6,544,484 B1
(45) Date of Patent: Apr. 8, 2003

(54) AEROSOL CHARGE ADJUSTING APPARATUS EMPLOYING A CORONA DISCHARGE

(75) Inventors: Stanley L. Kaufman, New Brighton, MN (US); Frank D. Dorman, Minneapolis, MN (US)

(73) Assignee: TSI Incorporated, St. Paul, MN (US)

( * ) Notice: Subject to any disclaimer, the term of this patent is extended or adjusted under 35 U.S.C. 154(b) by 0 days.

(21) Appl. No.: 09/596,159

(22) Filed: Jun. 16, 2000

Related U.S. Application Data

(60) Provisional application No. 60/140,033, filed on Jun. 18, 1999.

(51) Int. Cl.[7] .............................. B01J 19/26; B01J 19/08
(52) U.S. Cl. .................................. 422/186.04; 422/186
(58) Field of Search ..................... 422/186, 186.04, 422/186.07

(56) References Cited

U.S. PATENT DOCUMENTS

| | | | |
|---|---|---|---|
| 4,795,330 A | | 1/1989 | Noakes et al. ................. 425/6 |
| 4,829,996 A | | 5/1989 | Noakes et al. ............. 128/200.14 |
| 4,910,637 A | * | 3/1990 | Hanna ........................ 361/229 |
| 4,967,608 A | | 11/1990 | Yost ............................ 73/866 |
| 5,076,097 A | | 12/1991 | Zarrin et al. ................. 73/61.1 |
| 5,098,657 A | | 3/1992 | Blackford et al. ............. 422/73 |
| 5,247,842 A | | 9/1993 | Kaufman et al. ........... 73/865.6 |
| 5,447,763 A | | 9/1995 | Gehlke ....................... 428/34.1 |
| 5,650,203 A | | 7/1997 | Gehlke ....................... 428/34.1 |
| 5,766,560 A | * | 6/1998 | Cole ........................ 422/186.18 |
| 5,813,614 A | | 9/1998 | Coffee ........................ 239/690 |
| 5,869,831 A | | 2/1999 | De La Mora et al. ....... 250/288 |
| 5,873,523 A | | 2/1999 | Gomez et al. ................. 239/3 |

FOREIGN PATENT DOCUMENTS

| | | | | |
|---|---|---|---|---|
| WO | WO 00/17908 | * | 3/2000 | ............ H01J/49/04 |

OTHER PUBLICATIONS

"A Sonic Jet Corona Ionizer for Electrostatic Discharge and Aerosol Neutralization"; *Aerosol Science and Technology*; 20:31–41 (1994); Francisco J. Romay, Benjamin Y.H. Liu, David Y.H. Pui.

* cited by examiner

*Primary Examiner*—James J. Seidleck
*Assistant Examiner*—Thao Tran
(74) *Attorney, Agent, or Firm*—Larkin, Hoffman, Daly & Lindgren, Ltd.; Frederick W. Niebuhr, Esq.

(57) ABSTRACT

A system for analyzing aerosols incorporates a corona discharge ion generator with a positively or negatively charged corona discharge needle formed of platinum or a platinum alloy. A high speed (40–210 meter per second) air flow sweeps the ions away from the corona discharge, and propels the ions into a mixing chamber in a turbulent jet that encounters an aerosol, also provided to the mixing chamber. In one version of the ion generator, the ions are carried into the mixing chamber through an orifice formed in a positively or negatively biased plate. In another alternative, the aerosol droplets are electrostatically generated, and propelled into the mixing chamber as an aerosol jet that confronts the ion jet to enhance a mixing of the charged droplets and the ions. In this version the droplets are advantageously neutralized to leave predominantly singly charged positive and negative particles, to provide a neutralized aerosol particularly well suited for analysis with a mass spectrometer.

35 Claims, 10 Drawing Sheets

AEROSOL CHARGE ADJUSTING APPARATUS EMPLOYING A CORONA DISCHARGE

This application claims the benefit of priority based on Provisional Application No. 60/140,033 entitled "Aerosol Charge Adjusting Apparatus Employing a Corona Discharge," filed Jun. 18, 1999.

BACKGROUND OF THE INVENTION

The present invention relates to devices used to alter the electrical charge distributions of aerosols, and more particularly devices that utilize a corona discharge to generate ions, which then are merged with an aerosol to either charge or neutralize the aerosol.

The study of aerosols involves a variety of applications in which it is desired to adjust the charges on the particles or droplets of the aerosol. There are applications in which it is advantageous to provide a charge distribution in which positive and negatively charged particles counterbalance one another, i.e., an equilibrium charge distribution. In other applications, it is considered more important that a predominant number of the particles carry no charge. In yet further applications, researchers skew the charge distribution toward either the positive or the negative side, and in a more specific application of this type attempt to maximize the number of particles that carry a specific non-zero charge. Corona discharge can be used in all of these applications.

To produce a corona discharge, a non-uniform electrostatic field is established between an electrically conductive needle and a conductive structure proximate the needle, e.g., a plate or a tube surrounding the needle. Given a sufficient field strength, air near the needle experiences a breakdown and becomes conductive. In the conductive corona region, accelerated electrons collide with air molecules to create a dense cloud of free electrons and positive ions. If the needle is biased to a positive voltage relative to the surrounding structure, the electrons return to the needle while the positive ions stream away from the needle toward the adjacent structure. When the discharge needle is disposed within a gas stream, many of the ions do not reach the adjacent structure, but instead become entrained in the gas stream and are transported by the gas stream toward the aerosol. When the discharge needle is negatively biased, the free electrons leave the needle, some of them attaching to molecules of the gas to form negative ions, and are transported toward the aerosol by the gas stream.

In an increasing number of aerosol studies, it is desired to generate aerosols in which the particles are monodisperse, i.e., substantially uniform in size. For these applications, an electrospray nebulizer is preferred, due to its ability to generate small and uniform droplets. In an electrospray nebulizer, an electrically conductive liquid is supplied at a controlled rate to a capillary tube. A voltage differential between the capillary tube and a surrounding conductive wall creates an electrostatic field that induces a surface charge in the liquid emerging from the tube. Electrostatic forces disperse the liquid into a fine spray of charged droplets.

To produce the spray, the droplets are charged near the "Rayleigh" limit, i.e., near the charge at which electrostatic repulsion would overcome the surface tension that otherwise holds the droplet together. As each electrospray droplet evaporates, the charge density on its surface increases, eventually exceeding the Rayleigh limit, causing a disintegration of the droplet into smaller droplets. The droplet fragments in turn continue to evaporate and can experience further disintegration. As a result, the distribution of droplet sizes lacks the uniformity desired for analysis of residue within the droplets.

To counteract this tendency, the droplets are charge neutralized, beginning immediately or shortly after their formation. In one approach, disclosed in U.S. Pat. No. 5,247,842 (Kaufman, et al.), radioactive Polonium is placed inside a chamber through which the electrospray generated droplets travel as they evaporate. The Polonium produces radiation that ionizes air molecules, which in turn encounter the droplets and reduce their charge. This enhances uniformity of the droplets by counteracting their tendency to disintegrate due to electrostatic forces.

This approach yields a reproducible charge distribution by exposing the aerosol particles or droplets to a bipolar plasma of gas ions, both positive and negative, allowing the aerosol elements to reach a steady state of charge distribution. This distribution is useful because it is predictable and produces a large proportion of particles having no charge. This approach has disadvantages, however, in that the use of radioactive materials raises safety and regulatory concerns. The cost of radioactive Polonium is relatively high, and its half-life is relatively short. Further, although the level of ion production can be varied by partially shielding the radioactive material, the level of ionization cannot be precisely controlled.

In view of the above, ion generation through use of a corona discharge has been considered as an alternative method of neutralizing electrospray droplets. The corona discharge can generate unipolar (e.g., only negative) ions, and thus be configured to counteract the charge of the electrospray droplets. Alternatively, if both positive and negative ions are desired, corona discharge devices can have oppositely charged corona discharge needles, or a single corona discharge tip can be rapidly alternated between positively and negatively charged states.

A disadvantage of corona discharge devices is their tendency to generate aerosol particles. The problem is thought to arise from the removal of material from the discharge needle, the creation of highly reactive gaseous species at concentrations sufficient to allow their aggregation into particles, or a combination of these factors. In any event, aerosols generated by the corona discharge needle interfere with attempts to measure the aerosol under study. The tendency especially interferes with the analysis of extremely fine particles, i.e., particles having diameters of about ten nanometers or less.

Particle generation by corona discharge devices interferes with their use in semiconductor manufacturing clean rooms, because the particles can be large enough to contaminate silicone wafers during their processing. In recognition of the problem, U.S. Pat. No. 4,967,608 (Yost) a describes a test chamber for measuring particles larger than three nanometers in diameter emitted from a corona discharge device. U.S. Pat. No. 5,447,763 and U.S. Pat. No. 5,650,203, both issued to Gehlke, recommend selecting certain materials for corona discharge tips, e.g., titanium, aluminum, and other metals that form protective oxide layers. Silicone coated tips of these materials were favored. Platinum and tungsten also were considered, but said to show substantial particle production, and thus found unsatisfactory.

Recently, electrostatic generation of droplets has been considered as a source of aerosols subject to analysis by mass spectrometry, given the capability of generating aerosol droplets that are small (submicron) and monodisperse. In addition, the ability to rapidly and efficiently neutralize the aerosol, preferably to the point where the aerosol consists predominantly of singly charged particles, is a key factor when the aerosol is provided to a mass spectrometer. Although the aforementioned Kaufman patent discloses both the droplet generation and neutralizing beneficial in this regard, a more efficient and more controllable neutralizing of the aerosol would considerably enhance the utility of electrospray-ionization mass spectrometry.

Therefore, it is an object of the present invention to provide an aerosol system in which the charged droplets or charged particles are neutralized more rapidly and in a manner that affords more control over the degree of neutralizing.

Another object is to provide a corona discharge device capable of selectively altering the charge distributions of aerosols formed of extremely small droplets and particles, without generating its own detectable particles and thereby interfering with an analysis of the aerosol under study.

A further object is to provide an electrospray-ionization mass spectrometry system in which the electrostatically generated aerosol is effectively neutralized without requiring the use of radioactive materials.

Yet another object is to provide a corona discharge device particularly well suited for charging and neutralizing aerosols consisting of submicron droplets or particles.

SUMMARY OF THE INVENTION

To achieve these and other objects, there is provided a system for generating a charge-adjusted aerosol. The system includes an enclosure defining a mixing chamber, a first orifice for admitting an aerosol into the chamber, and a second orifice for admitting corona discharge ions into the chamber. The system further includes an electrostatic droplet generator having an electrostatic discharge adapted to generate multiple electrically charge droplets of a sample that includes an electrically conductive liquid and a nonvolatile material dispersed substantially uniformly throughout the liquid. An ion generator of the system has a corona discharge region electrically biased to generate multiple ions. A fluid passage is adapted for a coupling with a gas source to guide a first gas flow past the electrostatic discharge region. This allows the gas flow to entrain at least a portion of the charged droplets and form an aerosol of the sample, and to carry the entrained droplets into the mixing chamber through the first orifice to direct an aerosol jet into the chamber.

A second fluid passage is adapted for a coupling with a gas source to guide a second gas flow past the corona discharge region. This allows the second gas flow to entrain at least a portion of the ions and carry the entrained ions into the mixing chamber through a second orifice to direct an ion carrying jet into the mixing chamber. The aerosol jet and the ion carrying jet merge inside the mixing chamber in a turbulent flow that promotes the mixing of the charged droplets and the ions, to alter the droplet charges toward a neutralizing of the aerosol. The enclosure further defines an exit orifice permitting the aerosol to exit the mixing chamber after the altering of the droplet charges.

As used in this application, the term "neutralizing" refers to a reduction—not the complete removal—of the charges in the particles, droplets or other elements of the aerosol. In this sense, a "neutralized" aerosol can include both charged and neutral (uncharged) particles or droplets. An aerosol with an unbalanced electrical charge distribution can be neutralized in the sense of reducing the predominance of a positive (or negative) charge.

The degree of neutralization varies with the nature of the analytical application. Some applications require neutralization levels sufficient to prevent Coulomb disintegration of charged droplets as they evaporate. In other applications, droplet disintegration may be of no concern, but there may be a need to insure that the number of particles carrying more than a single charge is insignificant. Other applications might require a balanced charge distribution, with or without any limit on the number of charges carried by any given particle.

The preferred ion generator includes an electrically conductive needle providing the corona discharge region. The needle is mounted within an electrically conductive ion generating housing and electrically biased with respect to the housing to provide a corona current, preferably maintained within a range of 10–20 microamperes. The needle, at least along the corona discharge region, is formed of a noble metal, in particular either platinum or a platinum iridium alloy. Other metals of the platinum family may be suitable, although less preferred.

Several factors are believed to contribute to the virtual elimination of measurable particle generation by the corona discharge needle. These include the needle material, the relatively low corona current, and the relatively high velocity gas flow (usually air) past the needle. The rapid air flow tends to cool the discharge needle, which may be a key factor in preventing the particle generation of a platinum needle discussed in the aforementioned Gehlke patents. The airflow also may avoid or reduce the bombardment of the discharge needle tip by corona ions, which otherwise would tend to heat the tip, perhaps sufficiently to evaporate material and thereby generate particles. Furthermore, the active species formed in the corona discharge may be diluted by the rapid airflow before they can aggregate into particles. Finally, the lower corona current contributes to the reduced discharge needle temperature by generating less heat in the needle.

Along with the virtual elimination of corona generated particles, the present system provides for a more efficient and more controllable neutralizing of charged droplets. The turbulence caused by the merger of the aerosol and ion jets effectively mixes the charged droplets and the ions, considerably reducing the time required for a significant number of oppositely charged ions to encounter and reduce the charges of the droplets. The ability to adjust the degree of electrical charge or bias applied to the discharge needle affords a degree of control not available when radioactive ion sources are employed.

An additional advantage of the corona discharge needle in neutralizing electrospray droplets is that it provides a unipolar ion source. If desired, however, the corona discharge can provide a bipolar source of ions, either by providing two oppositely charged corona discharge needles in separate chambers, or by rapidly switching between alternative positive and negative biasing sources coupled to a single discharge needle.

When an aerosol jet and a single ion carrying jet are directed into the mixing chamber, the two jets preferably confront one another and travel in opposite directions towards one another to maximize the mixing potential. Preferably, the jets travel into the chamber at mean velocities of at least 40 meters per second, to insure rapid mixing within a turbulent flow. In an alternative embodiment, a second ion generator provides oppositely charged ions entrained in a third gas flow, resulting in a merger of the aerosol jet with two jets of ions, oppositely charged. In this arrangement, the ion jets are advantageously arranged to confront one another and thus travel in opposite directions while the aerosol jet is perpendicular to the ion jets.

Further in accordance with the invention, there is provided a device for adjusting the electrical charge distribution of an aerosol. An enclosure of the device defines chamber, a first orifice for entry of an aerosol flow, and a second orifice for entry of ions. The device includes an ion generator having a corona discharge region disposed proximate the second orifice and electrically biased to generate multiple ions. A fluid passage is adapted for a coupling with a gas source to guide a gas flow past the corona discharge region. Thus the gas flow entrains some of the first ions and carries the entrained ions into the chamber through the second orifice, to merge with an aerosol flowing into the chamber through the first orifice. When merging with the aerosol, the ions alter the electrical charge distribution of the aerosol. A conductive member is provided proximate the corona discharge region and the second orifice. The member is electrically biased, and has the same electrical polarity as the corona discharge region. The enclosure further has an exit orifice to allow aerosol to exit the enclosure after the electrical charge distribution is altered.

The preferred conductive member is a conductive plate, through which the second orifice is formed. The plate is charged or biased at a level considerably lower than that of the discharge needle, e.g., several hundred volts as compared to the 2,000 volt potential at the needle. Applying a negative charge to the plate, when the corona discharge needle also is negatively charged, has a significant impact. When the plate is negatively charged, the ions are capable of depositing sufficient negative charges on the aerosol particles to produce a larger peak for singly charged negative particles than for singly charged positive particles. The result is an increased fraction of the aerosol particles having a single negative charge, to more than 25 percent, depending on particle size, considerably higher than the fraction obtained by any other charging method. At the same time, a doubly-charged peak on the negative side is avoided, reducing the complexity of the mass spectrum in a manner not possible in systems using either radioactive source ionization, or negative-ion corona sources that lack the biased orifice plate.

Thus, in accordance with the present invention, aerosol analyzing systems can employ an improved corona discharge device that affords a more rapid and more effective altering of the electrical charge distribution of an aerosol, whether to charge or to neutralize the aerosol. The ionizer requires no radioactive ion source, and virtually eliminates the problem of small particle generation found in conventional corona discharge devices. In an electrospray-ionization mass spectrometry system utilizing the ionizer in combination with electrospray generated aerosols, extremely small particles with a charge distribution dominated by neutral and singly charged particles can be provided to the mass spectrometer for analysis.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
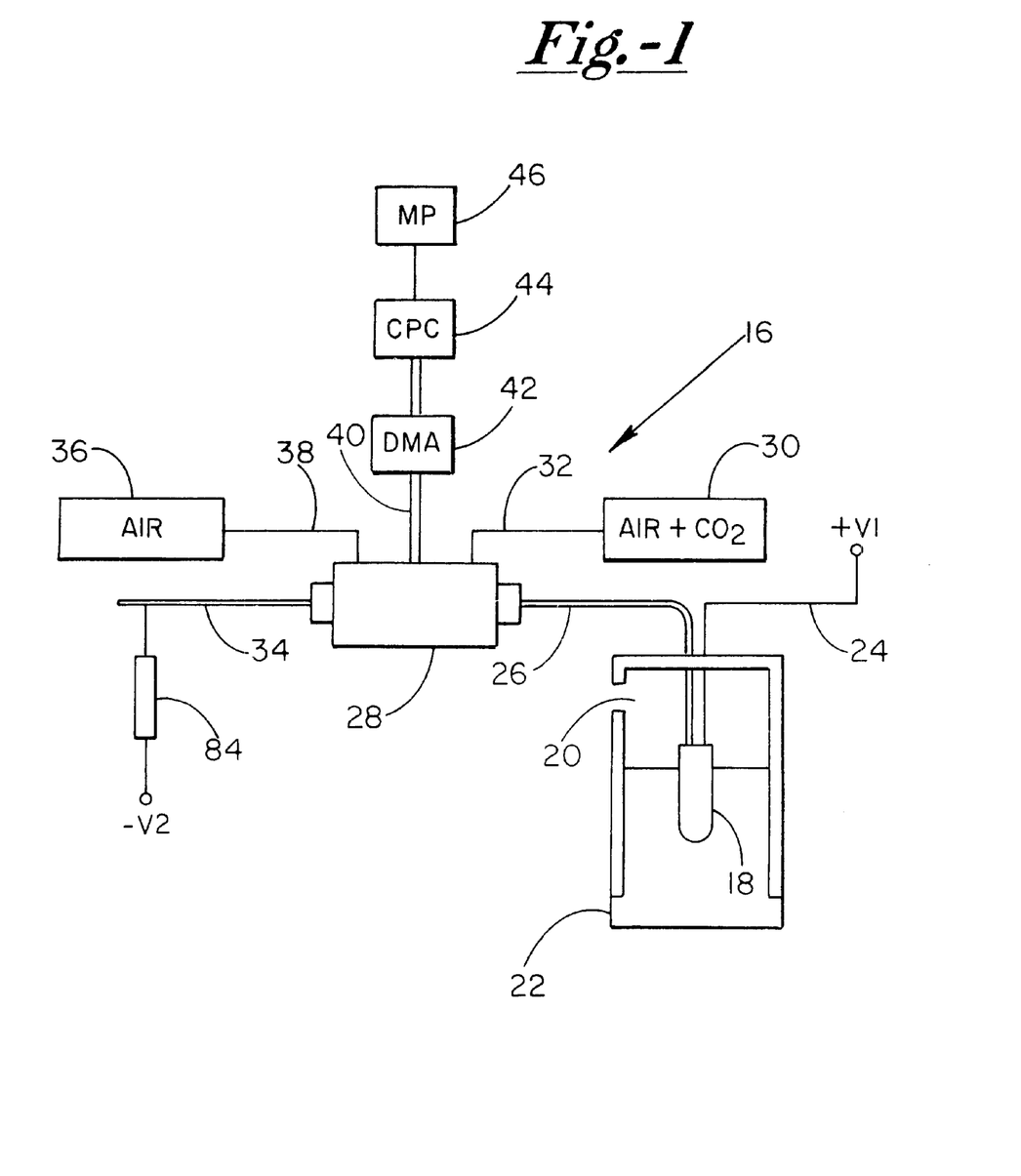
FIG. 1 is a schematic view of a system for analyzing electrostatically generated aerosols in accordance with the present invention.

Turning now to the drawings, there is shown in FIG. 1 a system 16 for analyzing particles composed of non-volatile material dispersed throughout a liquid in a particle-liquid solution or sample. The sample contains a volatile additive, such as ammonium acetate provided at about 20 millimoles per liter, to enhance its electrical conductivity. The sample is held in a vial 18, inside a chamber 20 of a container 22 surrounding and supporting the vial. An electrically conductive lead, preferably a wire 24 formed of platinum or another inert metal, has one end submerged in the liquid sample. The other end of the wire is coupled to a high positive voltage source +V1, typically in the range of 2,000–4,000 volts, to bias the sample at essentially the same voltage.

An electrospray capillary 26, submerged in the sample along with wire 24, is used to supply the sample to an aerosol neutralizing device 28 at a constant flow rate, typically in the range of 50–100 nanoliters per minute. Capillary 26 typically has a length of 25–30 centimeters, and an internal bore diameter of about 25 micrometers. The supply rate is controlled by controlling a pressure differential between the submerged end of the capillary and a spraying tip at the opposite end of the capillary. More particularly, pressure at the spraying tip is sensed, and any change is matched by varying the pressure in chamber 20 to maintain the pressure differential at a predetermined level, depending on the desired sample flow rate. The desired pressure differential varying with the desired flow rate, to a maximum of about 4 psi.

The generation of aerosol droplets based on the liquid sample requires a gas flow. To this end, a pressurized supply 30 of air augmented with carbon dioxide is provided to device 28 via a line 32. The air/$CO_2$ flow rate is selected within a range of 1–3 liters per minute, with the flow of $CO_2$ alone being about 0.1 liters per minute. Another electronegative gas, e.g. sulfur hexafluoride, can be used in lieu of $CO_2$ Neutralizing device 28 incorporates an ion generator including a corona discharge needle 34. The discharge needle is biased to a voltage of −V2, typically about 3,000 volts. A source 36 of clean, filtered air under pressure is coupled to device 28 via a line 38. The pressure of air supply 36 is predetermined to provide a steady flow in the range of 0.5–2.5 liters per minute, more preferably about 0.75 liters per minute.

The neutralized aerosol exits device 28 via a line 40 and proceeds to a differential mobility analyzer (DMA) 42. The DMA separates a portion of the aerosol particles from the remainder of the particles, based on electrical mobility, and can be configured to select either positively charged or negatively charged particles.

The output of the DMA is provided to a condensation particle counter (CPC) 44, also known as a condensation nucleus counter. In the CPC, the selected aerosol particles travel through a gas stream saturated with butyl alcohol or another volatile liquid, which condenses on the particles to "grow" each particle to a larger effective size for easier detection. U.S. Pat. No. 4,790,650 (Keady) describes a condensation particle counter. The output of CPC 44 is provided to a microprocessor 46 which provides information useful for analyzing the aerosol, e.g. concentration values. Alternatively, an electrometer can receive the DMA output. The aerosol is collected on a surface, and the resulting rate of charge arrival is measured as a current. For singly charged particles, this current is proportional to the aerosol concentration and flow rate.

Figure 2:
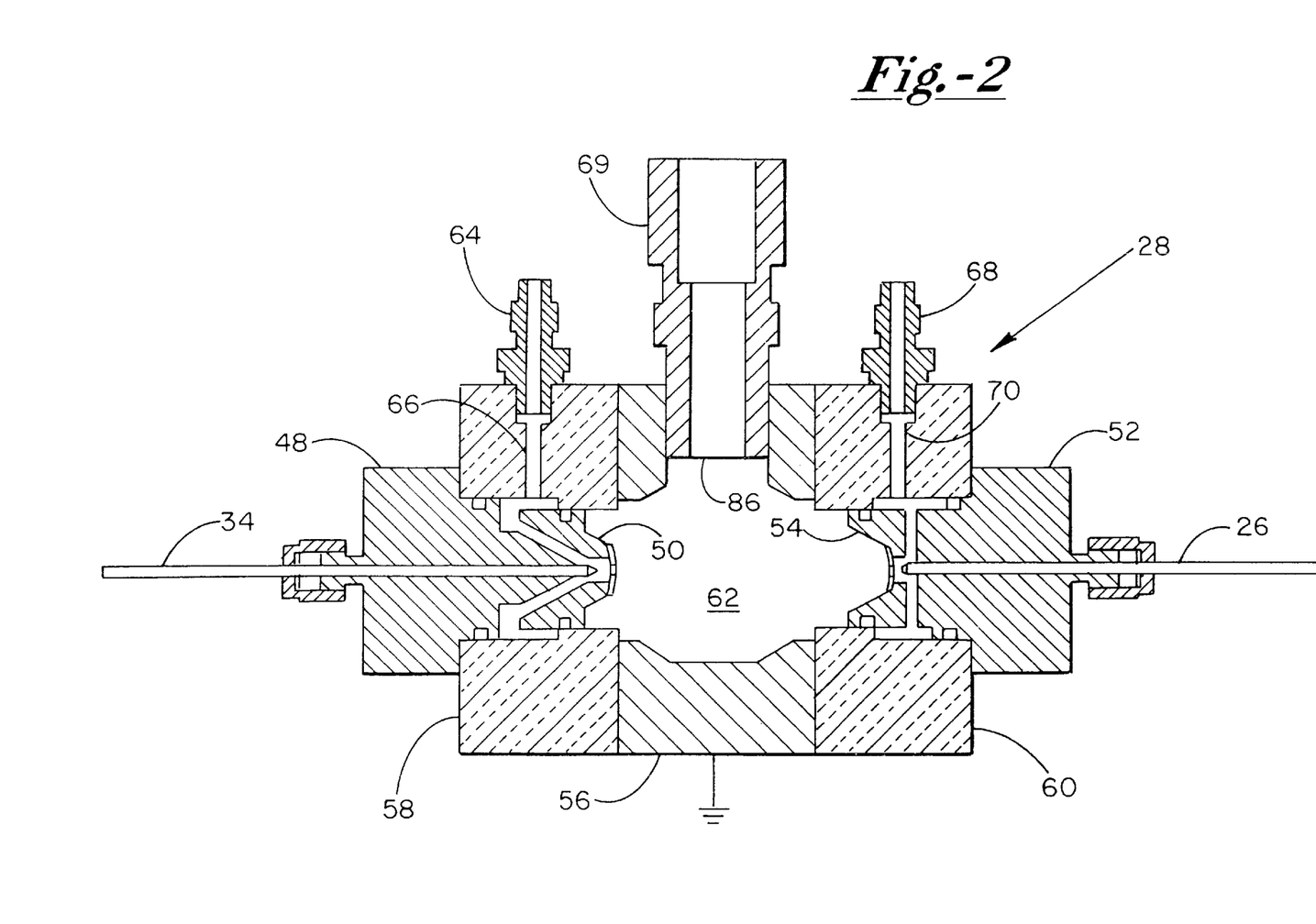
FIG. 2 is an enlarged sectioned view of an aerosol neutralizing device of the system.
Figure 3:
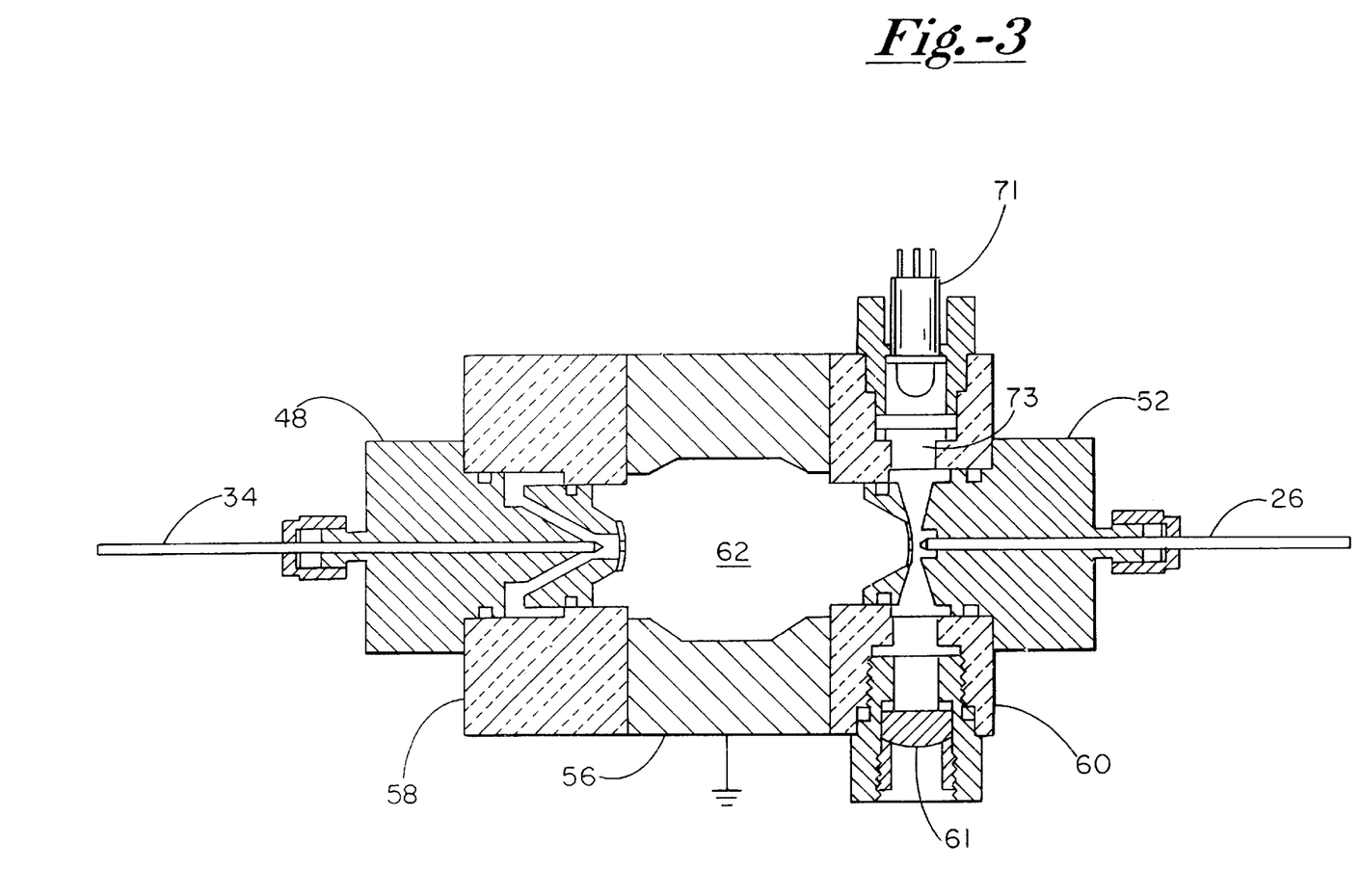
FIG. 3 is another enlarged sectional view of the neutralizing device.
Figure 4:
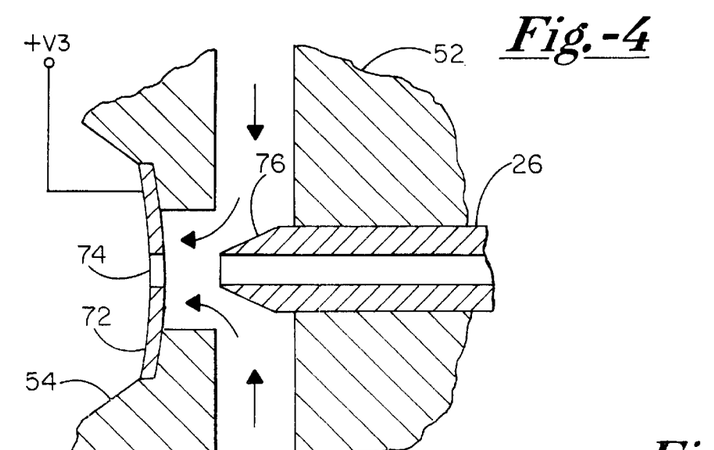
FIGS. 4–6 are enlarged schematic views of different portions of the neutralizing device.
Figure 5:
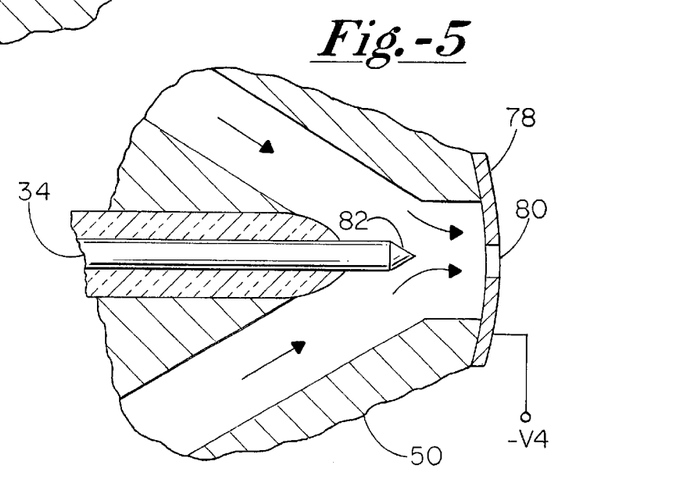

FIG. 2 illustrates several structural segments of neutralizing device 28. With reference to FIGS. 2 and 3, these include an ion generator housing segment 48, an ion orifice support segment 50 adjacent segment 48, a droplet generator housing segment 52, an electrospray orifice support segment 54 adjacent segment 52, and a medial segment 56. These segments are preferably formed of aluminum or stainless steel. Two insulative neutralizer body segments 58 and 60 are provided to electrically isolate the conductive segments from one another. The segments cooperate to define a mixing chamber 62 inside device 28.

A fitting 64 is mounted to segment 58, and cooperates with segments 48, 50 and 58 to form a fluid passage 66, through which air from source 36 and line 38 is guided into mixing chamber 62. Similarly, a fitting 68 cooperates with segments 52, 54 and 60 to form a fluid passage 70 for guiding the air/carbon dioxide mixture from supply 30 to the mixing chamber. A fitting 69 at the exit orifice is adapted for a coupling to a length of tubing -40 that carries the exit aerosol to the DMA.

As seen in FIG. 3, a 90 degree rotation relative to FIG. 2, the capillary tip is illuminated by a light emitting diod 71 through a passage 73 for viewing by an optical element 61 to form a magnified image of the spray tip. The sensed pressure near the tip is provided to a controller (not shown) that adjusts the pressure inside chamber 20 to maintain the desired pressure differential between the intake and spraying ends of the capillary.

With reference to FIG. 4, an electrically conductive electrospray orifice plate 72 is mounted to segment 54. An electrospray orifice 74 is formed through plate 72, and has a diameter of about 0.5 millimeters. A spray tip 76 of capillary 26 is axially spaced from orifice 74 a distance of about 0.5 millimeters.

As noted above, the liquid sample is biased at a positive voltage; selected within the range of 2,000–4,000 volts. Due to the conductivity of the liquid, the voltage at electrospray tip 76 of the capillary is essentially the same. Medial segment 56 electrically isolated from the capillary and segments 52 and 54, is maintained at ground. The result is an intense electrical field between electrospray tip 76 and the medial segment.

Consequently, as the liquid sample reaches the capillary tip, the liquid breaks up into small droplets (typically about 150 nanometers in diameter) that carry a relatively high charge, e.g. at least about 2,000 (e) units of charge. If desired, a positive bias +V3 can be applied to electrospray orifice plate 72, which is electrically isolated from medial segment 56 and spray tip 76.

Arrows in FIG. 4 indicate the direction of the gas (air and carbon dioxide) flow past the spray tip, through electrospray orifice 74 and into mixing chamber 62. Given the 0.5 millimeter diameter of orifice 74 and the gas flow rate of 1–3 liters per minute, the average linear velocity of the gas entering the chamber through the orifice is approximately 80–240 meters per second. The air/carbon dioxide mixture entrains the charged droplets as it flows rapidly past spray tip 76, thus forming an aerosol of the liquid sample. The aerosol is propelled into chamber 62 as a turbulent jet of the highly charged droplets.

As seen in FIG. 5, an electrically conductive ionization plate 78 is mounted to segment 50. A corona discharge orifice 80 is formed through plate 78, and has a diameter of about 0.5 millimeters. Needle 34 has a corona discharge tip 82 axially spaced apart from orifice 80 by about 0.5 millimeters. The arrow's in FIG. 5 indicate the flow of air past tip 82, and into the chamber through orifice 80. As noted previously, discharge needle 34 is biased to a negative 3,000 volts. Needle 34 is isolated from segment 48 by an insulative jacket. Accordingly, an intense electrical field is formed between discharge tip 82 and grounded medial segment 56. Ionization plate 78, electrically isolated from discharge tip 82 and segment 48, can be grounded or biased to a negative voltage −V4 if desired.

When ionization plate 78 is biased, it is biased at the same polarity as corona discharge needle 34, but at a considerably lower level, e.g. several hundred volts. A negative bias on the ion orifice plate, when the corona discharge needle also is negatively charged, enhances the production of singly charged negative particles.

The intense electrical field results in a corona discharge at the discharge tip forming electrons and positive ions. Given the negative bias of the discharge needle, the positive ions are drawn to the needle while the electrons are repelled, eventually attaching to molecules of the passing air flow to form negative ions entrained in the air flow. Given the air flow rate of 0.5–2.5 liters per minute, the mean linear velocity of the air flow (including the entrained ions) through the orifice into mixing chamber 62 is in the range of 40–210 meters per second. Accordingly, the negative ions are propelled into the chamber in the form of an ion carrying jet.

The negative bias to corona discharge needle 34 is provided through a high resistance 84 (100,000,000 ohms), to stabilize the corona current. Preferably the corona current is maintained within the range of 10–20 microamperes. The corona current level is low compared to that in many conventional corona discharge ionizers, and thus generates less heat in the corona discharge needle, a factor contributing to the considerable reduction in particles generated by the needle. Corona discharge tip 82 also remains cooler due to the rapid air flow past the discharge tip. Given the close proximity of the discharge tip to ionization orifice 80, the air flow velocity about the tip is substantially the same as the velocity through the orifice. Aside from the convective removal of heat from the corona discharge tip, the air flow is believed to further reduce the possibility of particle formation by sweeping ions, both positive and negative, away from the corona discharge before they are able to aggregate into particles.

Figure 6:
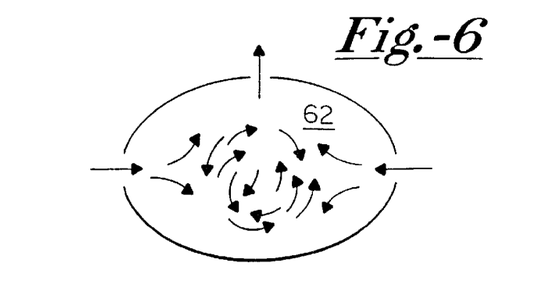

With orifice 74 and orifice 80 at opposite ends of mixing chamber 62, the ion carrying jet and the aerosol jet confront one another, traveling in opposite directions toward one another to a merger region within the mixing chamber. The jets intermingle with one another in a turbulent flow, which promotes a mixing of the positively charged aerosol droplets and the predominantly negatively charged ions. The result is a rapid and effective neutralization of the aerosol droplets. This result is seen from FIG. 6, where arrows schematically illustrate the confrontation of the aerosol and ion carrying jets and the resulting turbulence.

As the sample aerosol travels through mixing chamber 62, the liquid evaporates, with the result that the aerosol exiting the chamber through an exit orifice 86 (FIG. 2) consists primarily of uniformly sized residue particles of the material originally dispersed throughout the liquid. As the aerosol droplets evaporate, negative ions from the corona discharge needle transfer electrons to the droplets, reducing their positive charge. After evaporation is substantially complete, the negative ions operate similarly to further reduce the charges in the residue particles. Given a sufficient level of ion generation and residence time in mixing chamber 62, neutralizing progresses to the point that the residue particles are left predominantly with zero charge or with one net positive or negative charge. Neutralization based on the corona discharge, as compared to neutralization based on radioactive ion generating materials, is more efficient, perhaps largely due to the degree of mixing occasioned by the confronting aerosol and ionized air jets. The unipolar nature of the ionized air also may be a contributing factor. In any event, when a solution containing Ferritin (a protein) was analyzed using the corona discharge, forced convection neutralization, and also analyzed based on radioactive source neutralization, the number of counts in the peak Ferritin particle at a concentration of five parts per million was higher for the corona discharge neutralized sample, by a factor of about 1.5, when the respective aerosol outputs were provided to the same differential mobility analyzer.

Figure 7:
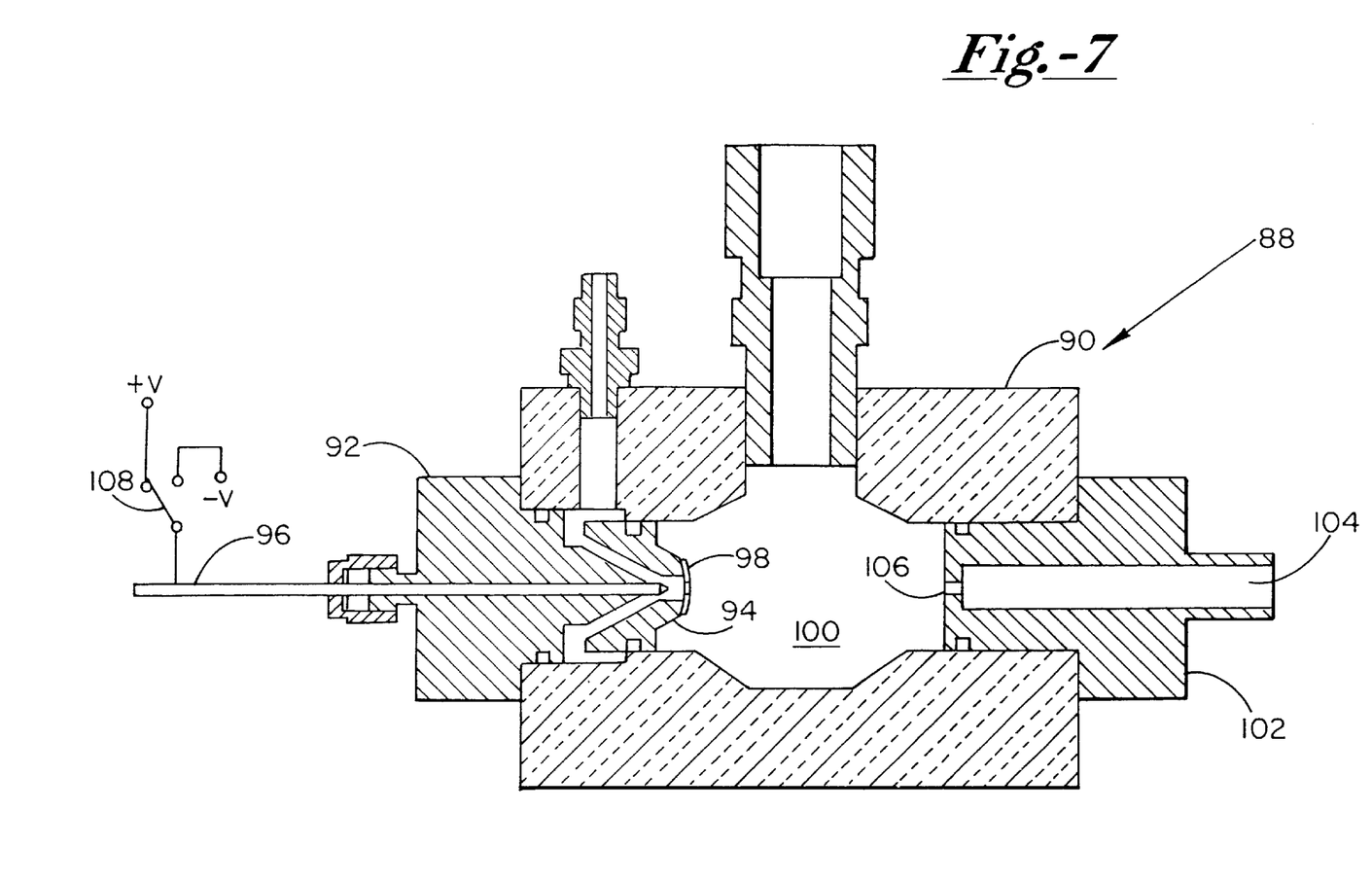
FIG. 7 is a sectioned elevation illustrating an aerosol charging/neutralizing device constructed according to the present invention.

FIG. 7 illustrates an alternative embodiment of the invention, in the form of an aerosol charging device 88. The device includes a primary body segment 90, an ion generating segment 92 and an ionization orifice segment 94 spaced apart from segment 92. A corona discharge needle 96 is mounted within segment 92, and has a corona discharge tip positioned near an ionization orifice, formed through an ionization plate 98 substantially as before.

On the opposite side of a mixing chamber 100, a segment 102 provides an aerosol passageway 104 in lieu of an electrospray capillary, with a narrow orifice 106 open to the mixing chamber. In this embodiment, the aerosol is generated by an alternative device (not shown) such as a pneumatic nebulizer or an ultrasonic nebulizer, or from another source such as an engine exhaust or the atmosphere. Accordingly, the aerosol is essentially neutral, or has an equilibrium electrical charge distribution, as it enters the mixing chamber. In this device, the corona discharge ions are intended to apply a predetermined charge distribution to the aerosol, rather than neutralize the aerosol.

In certain applications, it may be desired to impart a balanced charge distribution to the aerosol, or at least provide charges of both polarities. To this end, a first voltage source −V and a second voltage source +V are coupled to the corona discharge needle to a switch 108, operable to rapidly alternate the polarity at which needle 96 is charged. As a result, the corona discharge tip provides ions in alternating waves of positively and negatively charged ions. The opposite-polarity sources +V and −V can, but need not, have the same absolute voltage level.

Figure 8:
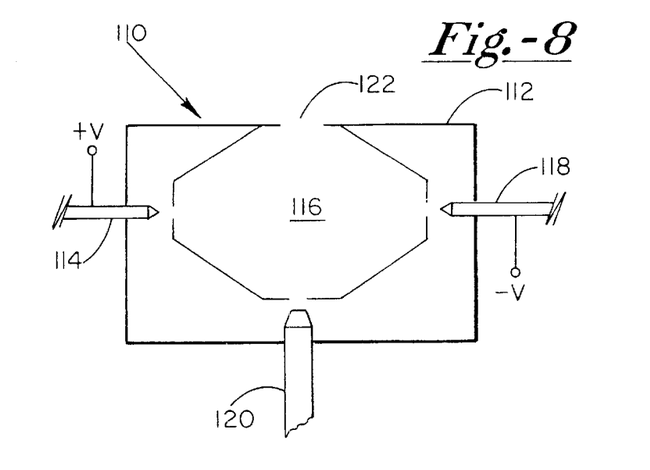
FIG. 8 is a sectioned elevation of an alternative embodiment charging/neutralizing device.

FIG. 8 schematically illustrates an alternative embodiment neutralizing/charging device 110 capable of simultaneously applying both positively charged ions and negatively charged ions to an aerosol. A body 112 of the device supports a positively biased corona discharge needle 114 on one side of a mixing chamber 116, and supports a negatively biased corona discharge needle 118 on the opposite side in confronting relation to needle 114. The neutralizer body also supports an aerosol source 120. On the opposite side of the chamber from the aerosol source is an exit orifice 122. Respective fluid flow passageways are provided in connection with the aerosol source and each of the ion generators, to provide two confronting ion containing jets, and an aerosol jet perpendicular to the ion jets. To adjust the proportion of positive ions to negative ions, the respective levels +V and −V can be varied.

Figure 9:
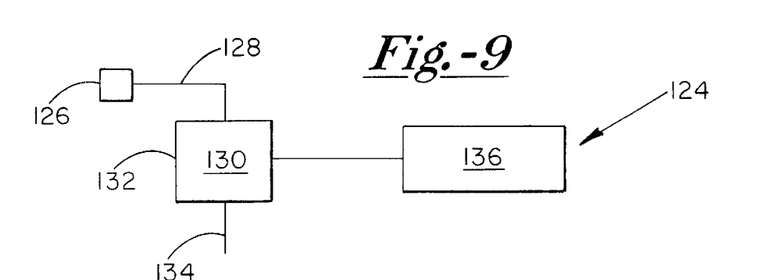
FIG. 9 is a schematic view of an alternative embodiment electrospray-ionization mass spectrometry system.

FIG. 9 illustrates an alternative embodiment in the form of an electrospray-ionization mass spectrometry system 124. System 124 includes an electrospray nebulizer 126 that provides charged electrospray droplets from a capillary 128 to the mixing chamber 130 of a neutralizing device 132. A corona discharge needle 134 provides negatively charged ions to the mixing chamber. The negatively charged ions are generated at a level sufficient to substantially neutralize the positively charged aerosol droplets, in the sense of providing a predominance of singly charged positive and negative droplets in the exit aerosol.

The exit aerosol is provided to a mass spectrometer 136. Because the residue particles reaching mass spectrometer 136 are singly charged, the resulting mass spectrum is simplified, due to an avoidance of the auxiliary peaks generated by particles carrying multiple charges.

Figure 10:
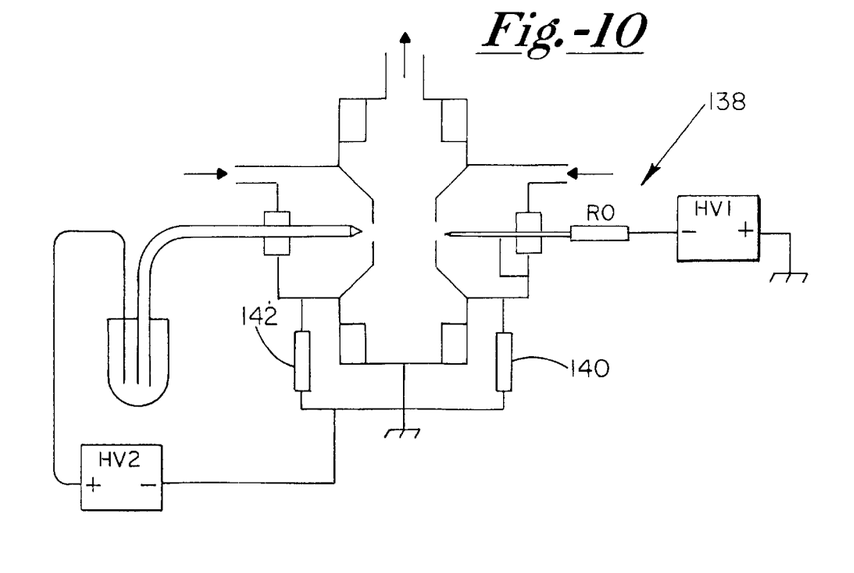
FIG. 10 is a schematic view of an alternative embodiment system for neutralizing an electrospray generated aerosol.

FIG. 10 illustrates an alternative embodiment aerosol neutralizing system 138, that differs from system 16 in that voltages +V3 and −V4, to the electrospray orifice plate and to the ionization plate respectively, are not provided through independent voltage sources. Rather, a negative bias is applied to the ionization plate by passing the corona current through a resistor 140, and a positive bias is applied to the electrospray plate by passing the electrospray current through a resistor 142.

Figure 11:
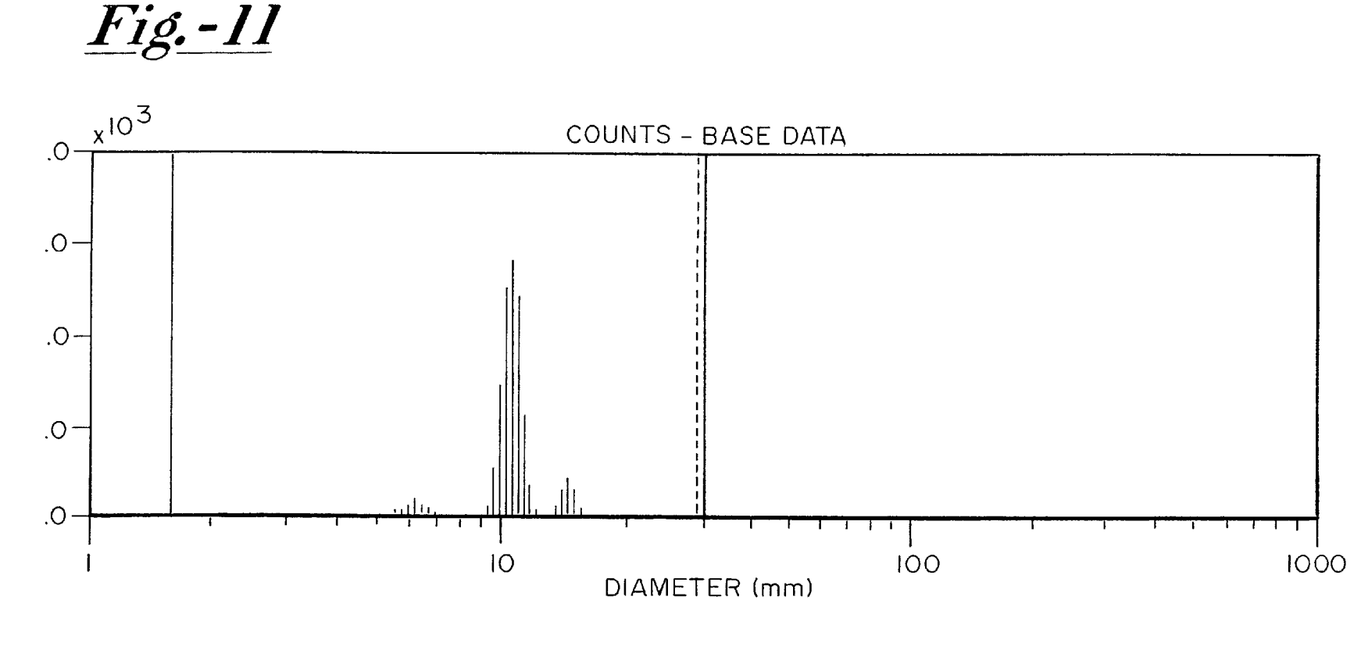
FIGS. 11 and 12 illustrate electrical charge distributions of aerosols generated by a aerosol neutralizing device of the type shown in FIGS. 2 and 3.
Figure 12:
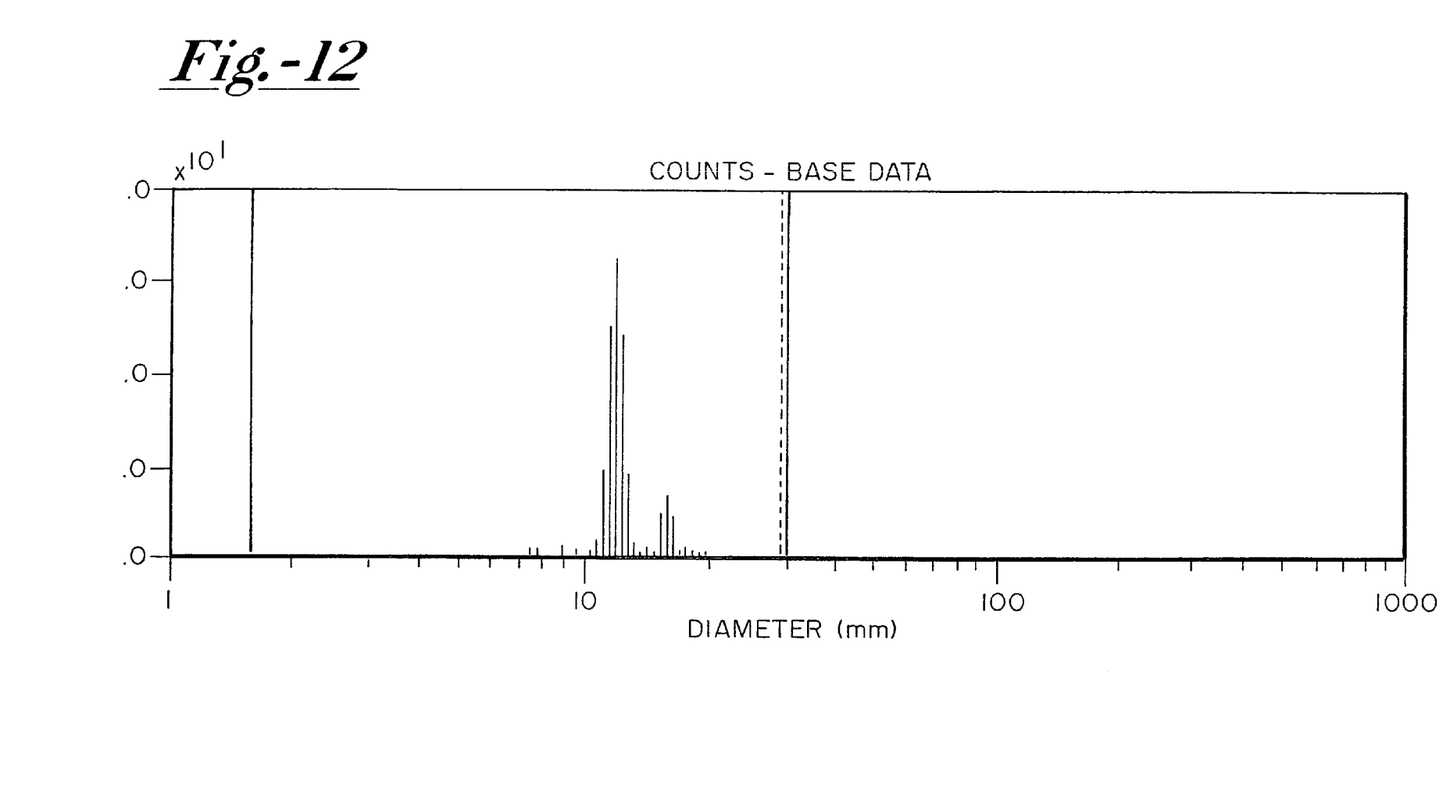

FIGS. 11 and 12 illustrate two runs on a scanning mobility particle sizer, with positively charged and negatively charged center rods, respectively. FIG. 11, associated with the negative rod, shows a peak of about 6,000 counts. FIG. 12, associated with the positive rod, shows a peak of only about 60 counts. Thus, corona discharge neutralizing reduces the positive charge to one net charge with a very narrow charge distribution. The residue is left mostly with charged particles of one positive charge, indicating a high efficiency in preventing highly charged droplets from being lost as they pass through the orifice, and the ability to control the ratio of positive and negative particles.

Figure 13:
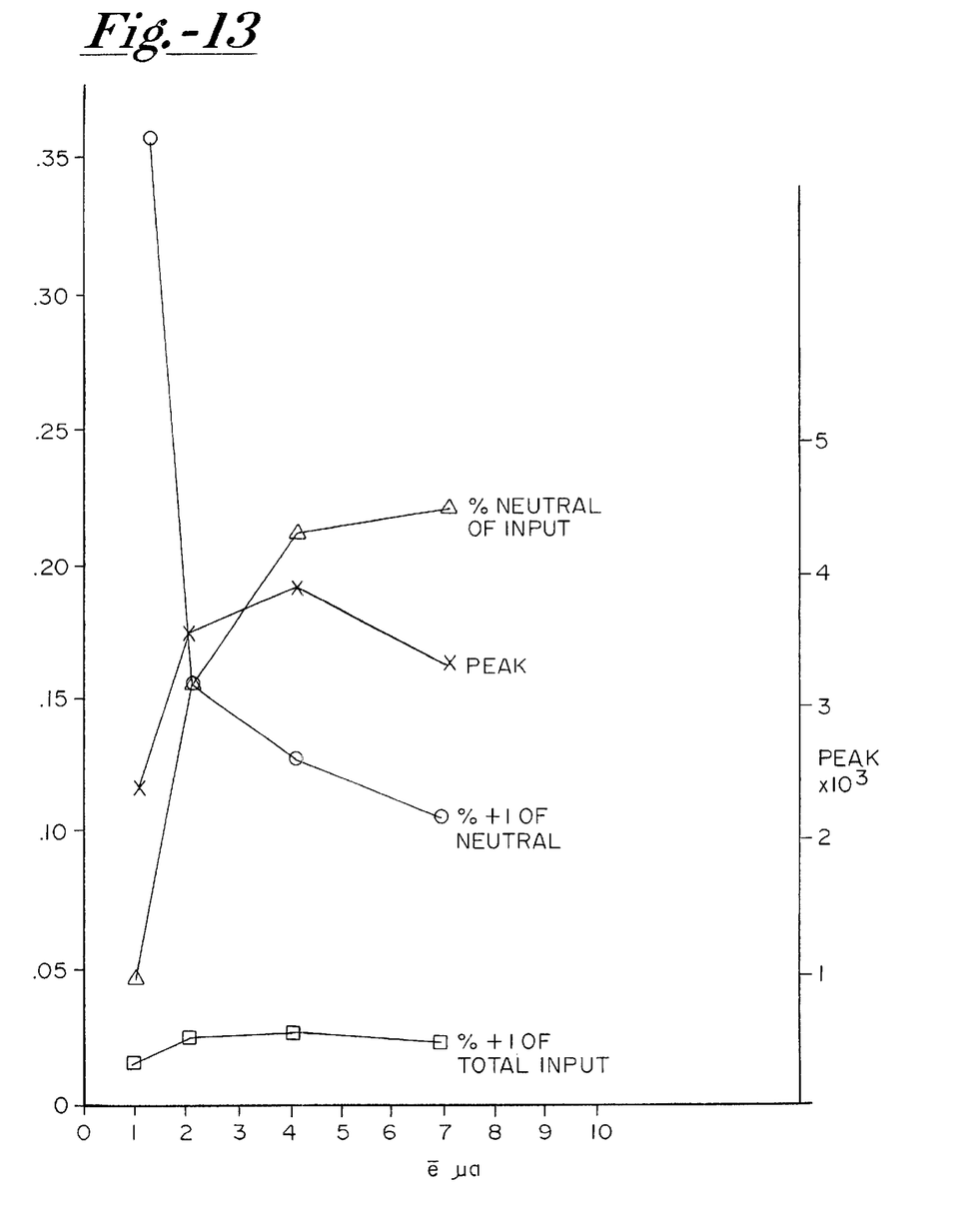
FIG. 13 is a chart showing efficiency of delivering neutral and singly charged positive particles as a function of ionization current.

The chart in FIG. 13 illustrates an increase in the efficiency of producing neutral particles as the ionization current increases.

Figure 14:
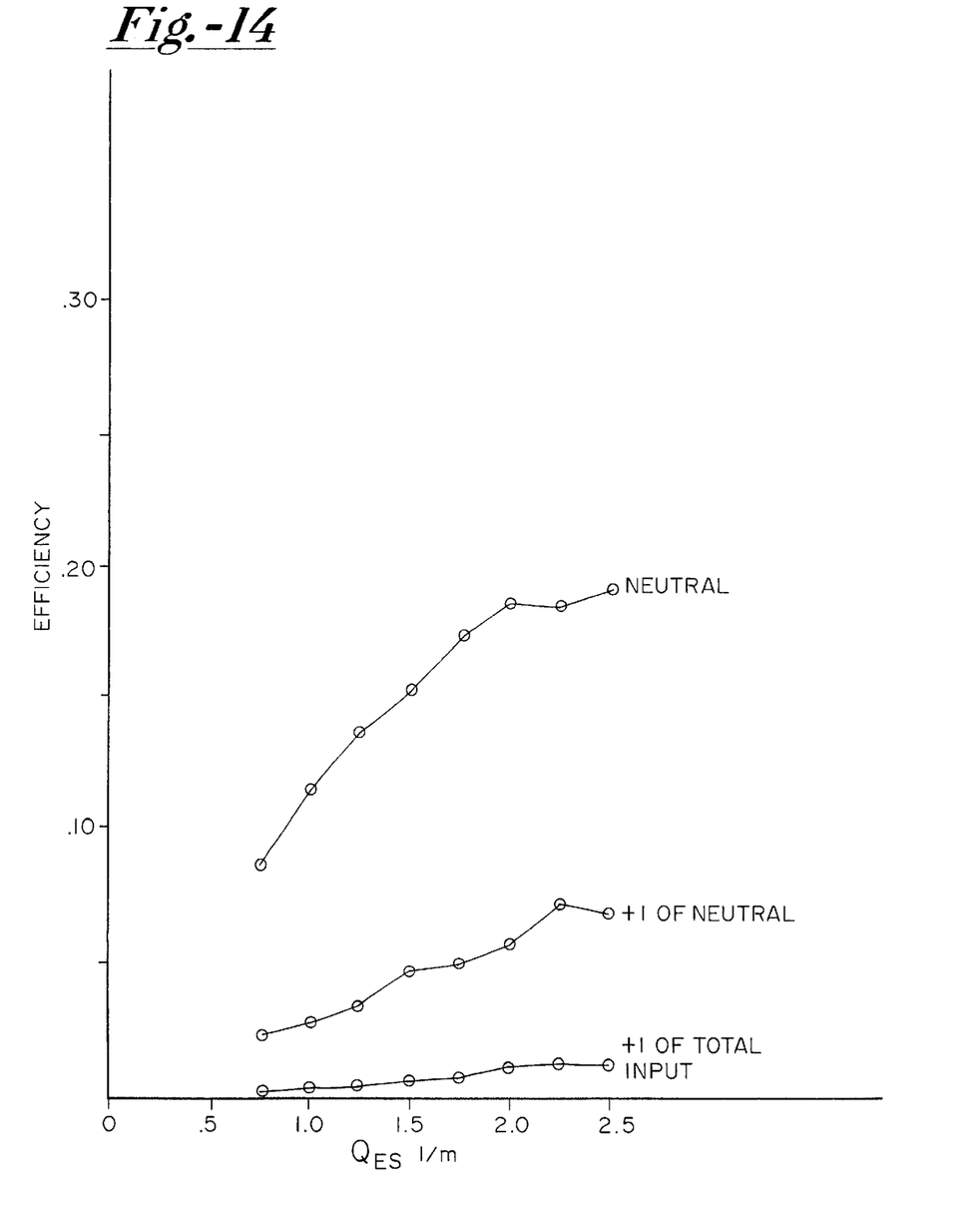
FIG. 14 is a chart showing efficiency of delivering neutral and singly charged positive particles as a function of the electrospray flow rate.

The chart in FIG. 14 illustrates an increase in efficiency of producing neutral and singly charged positive particles as the electrospray flow rate increases.

A salient feature of the present invention is the capability of tailoring the manner in which the charged distribution of an aerosol is altered, whether by charging or by neutralizing the aerosol. In addition to the ionization current and the electrospray flow rate, parameters that can be varied include the gas flow rates through the electrospray orifice and the ionization orifice, the proximity of the confronting ion and aerosol jets, the size of the mixing chamber, and the magnitude of the electrical bias applied to the ionization orifice plate and the droplet orifice plate.

Thus in accordance with the present invention, a more controlled and more efficient level of charging and neutralization are achieved, while the use of radioactive materials is avoided. Particle generation by the corona discharge tip is essentially eliminated, enabling a more accurate analysis of extremely fine particles.

What is claimed is:

1. A system for generating a charge-adjusted aerosol, including:

an enclosure defining a mixing chamber, a first orifice for admitting an aerosol into the chamber, and a second orifice for admitting corona discharge ions into the chamber;

an electrostatic droplet generator having an electrostatic discharge region adapted to generate multiple electrically charged droplets of a sample including an electrically conductive liquid and a non-volatile material dispersed substantially uniformly throughout the liquid;

a first ion generator having a first corona discharge region electrically biased to generate multiple first ions;

a first fluid passage adapted for a coupling with a gas source to guide a first gas flow past the electrostatic discharge region to entrain at least a portion of the charged droplets and form an aerosol of the sample, and to carry the entrained droplets into the mixing chamber through the first orifice to direct an aerosol jet into the mixing chamber; and a second fluid passage adapted for a coupling with a gas source to guide a second gas flow past the corona discharge region to entrain at least a portion of the first ions and carry the entrained ions into the mixing chamber through the second orifice to direct a first ion carrying jet into the mixing chamber;

wherein the aerosol jet and the first ion carrying jet merge inside the mixing chamber in a turbulent flow that promotes a mixing of the charged droplets and the first ions, to alter the droplet charges toward a neutralizing of the aerosol; and wherein the enclosure further defines an exit orifice permitting the aerosol to exit the mixing chamber after said altering of the droplet charges.

2. The system of claim 1 wherein:
   the electrically charged droplets, during said altering, also are reduced in size by evaporation of the liquid.

3. The system of claim 2 wherein:
   the evaporation is substantially complete while the aerosol is inside the mixing chamber, whereby the aerosol exits the chamber as a stream of particles consisting essentially of the non-volatile material.

4. The system of claim 2 wherein:
   the charged droplets are monodisperse, and said altering proceeds at a rate sufficient to prevent the charged droplets from disintegrating due to repulsive Coulombic forces as they evaporate, whereby the aerosol remains substantially monodisperse as it exits the enclosure.

5. The system of claim 1 further including:
   an aerosol characterizing device disposed to receive the aerosol from the enclosure.

6. The system of claim 5 wherein:
   the aerosol characterizing device is selected from the group of devices consisting of: a differential mobility analyzer in combination with either a condensation nucleus counter or an electrometer; and a mass spectrometer.

7. The system of claim 1 wherein:
   the enclosure includes an electrically conductive plate, the second orifice is formed through the plate, and the plate and the corona discharge region are electrically biased to the same electrical polarity.

8. The system of claim 7 wherein:
   the electrically conductive plate and the corona discharge region are negatively biased.

9. The system of claim 1 wherein:
   the aerosol jet and the ion carrying jet are oppositely directed.

10. The system of claim 1 wherein:
    the first ion carrying jet travels past the corona discharge region at a mean velocity of at least about 40 meters per second, and the corona discharge region is spaced apart from the second orifice by a distance of less than one millimeter.

11. The system of claim 10 wherein:
    the aerosol jet is directed into the neutralization chamber at a mean velocity through the first orifice of at least about 40 meters per second.

12. The system of claim 1 wherein:
    the first ion generator includes an electrically conductive needle providing the corona discharge region, mounted within an electrically conductive ion generator housing and electrically biased with respect to said housing.

13. The system of claim 12 wherein:
    the needle, at least along the corona discharge region, is formed of a noble metal.

14. The system of claim 1 wherein:
    the droplet generator includes a capillary having a first end submerged in the liquid sample and a second end region comprising the electrostatic discharge region and mounted within an electrically conductive droplet generator housing; and
    the liquid sample at the electrostatic discharge region is electrically biased with respect to the housing.

15. The system of claim 14 wherein:
    the first gas flow includes air, and further includes an electronegative gas selected from the group consisting of carbon dioxide and sulfur hexafluoride and provided at a flow rate off at least about three percent of the first gas flow.

16. The system of claim 1 further including:
    a second ion generator having a second corona discharge region disposed proximate the enclosure and biased to an electrical polarity opposite that of the first corona discharge region, thereby to generate multiple second ions and oppositely charged with respect to the first ions;
    a third fluid passage adapted for a coupling with a gas source to guide a third gas flow past the second corona discharge region to entrain at least a portion of the second ions and carry the entrained ions into the mixing chamber through a third orifice to direct a second ion carrying jet into the chamber;

wherein the second ion carrying jet is oriented to merge with the first ion carrying jet and the aerosol jet in said turbulent flow.

17. The system of claim 16 wherein:

the first and second ion carrying jets are oppositely directed, and the aerosol jet is substantially perpendicular to the ion jets.

18. A device for adjusting the electrical charge distribution of an aerosol, including:

an enclosure defining a chamber, a first orifice to permit an aerosol to flow into the chamber from outside of the enclosure, and a second orifice permitting entry of ions into the chamber;

a first ion generator electrically biased to generate multiple first ions at at a first corona discharge region thereof disposed proximate the second orifice;

a first fluid passage adapted for a coupling with a gas source to guide a first gas flow past the first corona discharge region to entrain at least a portion of the first ions having a selected electrical polarity and to carry the entrained ions into the chamber through the second orifice, to merge with an aerosol flowing into the chamber through the first orifice, thus to alter an electrical charge distribution of the aerosol; and a conductive member proximate the second orifice, forming part of the enclosure and electrically isolated from a remainder of the enclosure whereby the conductive member is adapted to be electrically biased relative to said remainder of the enclosure;

wherein the enclosure further defines an exit orifice to allow the aerosol to exit the enclosure after the electrical charge distribution is altered.

19. The device of claim 18 wherein:

the conductive member comprises a conductive plate electrically biased to have said selected electrical polarity, and the second orifice is formed through the conductive plate.

20. The device of claim 18 further including:

a second ion generator having a second corona discharge region electrically biased to a polarity opposite to that of the first ion generator to generate multiple second ions charged oppositely from the first ions; and a second fluid passage adopted for a coupling to a gas source to guide a second gas flow past the second corona discharge region to entrain at least a portion of the second ions and carry the entrained ions into the chamber through a third orifice.

21. The device of claim 18 wherein:

the first gas flow and the entrained first ions travel through the second orifice into the chamber at a mean velocity of at least about 40 meters per second.

22. The device of claim 18 further including:

a switching means for selectively changing the polarity of the electrical bias applied to the corona discharge region.

23. The device of claim 18 further including:

a droplet generator adapted to generate multiple droplets of a liquid sample that includes a non-volatile material substantially uniformly dispersed throughout the liquid, the droplet generator having an electrostatic discharge region at which the droplets are generated; and a second fluid passage adapted for a coupling to a gas source to guide a second gas flow past the electrostatic discharge region to entrain at least a portion of the droplets to provide said aerosol as an aerosol of the liquid sample, and to carry the entrained droplets into the chamber through the first orifice to merge with the first gas flow including the entrained first ions.

24. The device of claim 23 wherein:

the aerosol, and the first gas flow including the entrained first ions, are provided through the first and second orifices, respectively, at mean velocities sufficient to provide respective aerosol and ion carrying jets, whereby the merger of the jets promotes a mixing of the droplets and the first ions to enhance the efficiency at which the electrical charge distribution of the aerosol is altered.

25. The device of claim 18 wherein:

the first ion generator includes an electrically conductive discharge needle mounted within and electrically isolated from an electrically conductive ion generator housing, and electrically biased with respect to the housing.

26. The device of claim 25 wherein:

the discharge needle, at least along the corona discharge region, is formed of a noble metal.

27. An electrospray-ionization mass spectrometry system, including:

an enclosure defining a mixing chamber, a first orifice for admitting an aerosol to the chamber, a second orifice for admitting corona discharge ions into the chamber, and an exit orifice for permitting the neutralized aerosol to exit the enclosure;

an electrostatic droplet generator having an electrostatic discharge region adapted to generate multiple electrically charged droplets of a liquid sample that includes a liquid and a non-volatile material dispersed substantially uniformly throughout the liquid;

an ion generator having a corona discharge region electrically biased to generate multiple ions at the corona discharge region;

a first fluid passage adapted for a coupling with a gas source to guide a first gas flow past the electrostatic discharge region to entrain at least a portion of the charged droplets and form an aerosol of the sample, and to carry the entrained droplets into the mixing chamber through the first orifice;

a second fluid passage adapted for a coupling with a gas source to guide a second gas flow past the corona discharge region to entrain at least a portion of the ions and carry the entrained ions into the mixing chamber through the second orifice, to merge with the aerosol to mix the charged droplets and the ions and thereby alter the droplet charges toward a neutralizing of the aerosol; and a mass spectrometer disposed to receive the aerosol after it exits the enclosure.

28. The device of claim 27 wherein:

the electrically charged droplets, during the altering of the droplet charges, also are reduced in size due to evaporation of the liquid.

29. The device of claim 28 wherein:

the evaporation is substantially completed while the aerosol is inside the mixing chamber, whereby the aerosol exits the chamber as a stream of particles consisting substantially of the non-volatile material.

30. The system of claim 28 wherein:

the charged droplets are monodisperse, and the charge altering proceeds at a rate sufficient to prevent the charged droplets from disintegrating due to repulsive Coulombic forces as they evaporate, whereby the aerosol remains monodisperse as it exits the enclosure.

31. The device of claim 27 wherein:

the enclosure includes an electrically conductive plate, the second orifice is formed through the plate, and the plate and the corona discharge region are electrically biased and have the same electrical polarity.

32. A corona discharge device for altering an electrical charge distribution of an aerosol, including:

an enclosure defining a chamber, a first orifice to permit an aerosol to flow into the chamber, a second orifice to permit corona discharge ions to enter the chamber, and an exit orifice;

an ion generator including an electrically conduction corona discharge needle having a corona discharge region disposed proximate the second orifice and electrically biased to generate multiple ions, wherein the discharge needle at least along the corona discharge region is formed of a noble metal; and a fluid passage adapted for a fluid coupling a gas source to guide as gas flow past the corona discharge region to entrain at least a portion of the ions and to carry the entrained ions into the chamber through the second orifice at a mean velocity of at least about 40 meters per second, to encounter and merge with an aerosol flowing into the chamber through the first orifice, thus to alter an electrical charge distribution of the aerosol.

33. The device of claim 32 wherein:

the noble metal is selected from the group consisting of: platinum, an alloy including platinum and iridium, and gold.

34. The device of claim 32 further including:

an electrically conductive member proximate the corona discharge region and the second orifice electrically biased and having the same electrical polarity as the corona discharge region.

35. The device of claim 32 further including:

a switching means for selectively changing the electrical polarity of the bias applied to the corona discharge needle.

* * * * *